(12) United States Patent
Astolfi et al.

(10) Patent No.: US 8,722,603 B2
(45) Date of Patent: *May 13, 2014

(54) TOILET SOAP WITH IMPROVED LATHER

(71) Applicant: Conopco, Inc., Englewood Cliffs, NJ (US)

(72) Inventors: Rafael Astolfi, Sao Paulo (BR); Andre Messias Krell Pedro, Sao Paulo (BR); Sergio Roberto Leopoldino, Sao Paulo (BR)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/922,764

(22) Filed: Jun. 20, 2013

(65) Prior Publication Data

US 2013/0281343 A1   Oct. 24, 2013

Related U.S. Application Data

(62) Division of application No. 13/625,273, filed on Sep. 24, 2012, now Pat. No. 8,492,323.

(60) Provisional application No. 61/563,194, filed on Nov. 23, 2011.

(51) Int. Cl.
   *A61K 8/00* (2006.01)

(52) U.S. Cl.
   USPC ............ 510/141; 510/152; 510/153; 510/481

(58) Field of Classification Search
   None
   See application file for complete search history.

(56) References Cited

U.S. PATENT DOCUMENTS

| 3,043,778 | A | 7/1962 | Kelly | |
| 5,264,144 | A | 11/1993 | Moroney et al. | |
| 5,540,852 | A * | 7/1996 | Kefauver et al. | ............ 510/152 |
| 5,656,579 | A | 8/1997 | Chambers | |
| 2007/0213247 | A1 | 9/2007 | Fenyvesi et al. | |
| 2009/0286706 | A1 | 11/2009 | Chakrabarty et al. | |

FOREIGN PATENT DOCUMENTS

| GB | 1287625 A | 9/1972 |
| WO | 9304161 | 3/1993 |

OTHER PUBLICATIONS

PCT International Search Report and Written Opinion on International Application No. PCT/EP2012/073008 dated Feb. 27, 2013.

* cited by examiner

*Primary Examiner* — Necholus Ogden, Jr.
(74) *Attorney, Agent, or Firm* — Ronald A. Koatz

(57) ABSTRACT

The present invention relates to soap bars having improved lather. Specifically, by limiting amounts of myristic acid and keeping specifically defined ratios of sum of $C_8$-$C_{10}$ fatty acids to $C_{12}$ fatty acid bars having substantially improved lather and unexpectedly obtained.

13 Claims, No Drawings

TOILET SOAP WITH IMPROVED LATHER

RELATED APPLICATIONS

This application is a divisional of 13/625,273, now U.S. Pat. No. 8,492,323.

BACKGROUND OF THE INVENTION

Soap bars for cleansing, are typically prepared by saponification/neutralizing triglyceride/fatty acids. In this saponification process, various fats (e.g., tallow, palms and coconut oil blends) are saponified in the presence of alkali (typically NaOH) to yield alkaline salts of fatty acid (derived from the fatty acid chains forming the glyceride) and glycerol. Glycerol is then typically extracted with brine to yield dilute fatty acid soap solution containing soap and aqueous phase (e.g., 70% soap and 30% aqueous phase). The soap solution is then typically dried (e.g., to about 12% water) and the remaining, mass is milled, plodded and stamped into bars. Alternatively, the soap solution can be cast in to moulds, blisters etc.

The chain length of fatty acid soaps varies depending on starting fat or oil feedstock (for purposes of this specification, "oil" and "fat" as used interchangeably, except where context demands otherwise). Longer chain fatty acid soaps (e.g., $C_{16}$ palmitic or $C_{18}$ stearic) are typically obtained from tallow and palm oils, and shorter chain soaps (e.g., $C_{12}$ lauric) may typically be obtained from, for example, coconut oil or palm kernel oil. The fatty acid soaps produced may also be saturated or unsaturated (e.g., oleic acid).

Typically, longer molecular weight fatty acid soaps (e.g., $C_{14}$ to $C_{22}$ soaps) are insoluble and do not generate foam, despite the fact that they can help making the foam generated by other soluble soaps creamier and more stable. Conversely, shorter molecular weight soaps (e.g., $C_8$ to $C_{12}$) lather quickly. However, the longer chain soaps are desirable in that they maintain structure and do not dissolve as readily. Unsaturated soaps (e.g., oleic) are soluble and lather quickly, like short-chained soaps, but form a denser, creamier foam, like the longer chained soaps.

Generally, particularly because of the structuring required to produce and maintain a solid soap bar structuring is provided by longer chain-length soaps) the production of a pure soap bar having enhanced lathering benefit (e.g., quick lather) is considered extremely difficult.

When synthetic surfactant (e.g., nonionic surfactant) is added to enhance mildness, typically the soap bar must still be predominantly made of long-chain soaps to ensure the bar is well structured and can maintain structure in stamping.

WO 93/04161 (P&G), for example, discloses bars comprising mixtures of soap, $C_{14}$-$C_{20}$ alkyl polyethoxylate nonionic and $C_{16}$-$C_{18}$ acyl isethionate (also a mild surfactant). The soap used comprises at least tallow (longer chain, slower lather) and includes cationic polymeric skin mildness aids and, as moisturizers, free fatty acid.

To overcome poor lathering problems, references in the art have disclosed use of specially tailored soaps (which involved additional. expensive processing) and/or use of additional, expensive co-actives, U.S. Pat. No. 5,540,852, Kefauver et al., for example, discloses a mild, lathering personal cleansing soap bar composition comprising from 30 to 85 by wt. tailored fatty acid soap comprising in turn from 50% to 85% of saturated fatty acid soap selected from the group consisting of: myristic, palmitic, and stearic acid soaps. Kefauver fails to disclose that minimum levels of capric and lauric fatty acid soaps and maximum levels of myristic fatty acid are required for enhanced lather.

U.S. Pat. No. 5,656,579, Chambers et al. discloses a mild toilet soap bar comprising blends of soap with one or more coactives, comprising at least 25% wt. on total actives of lauric acid soaps. Again, Chambers fails to disclose soap bar formulations having low amounts of myristic acid soap, or having levels of capric and lauric fatty acid soaps as claimed in our invention.

Thus, previous attempts for enhance mildness and/or in-use performance are provided by specialized tailoring or use of expensive co-actives.

Nowhere is there disclosed compositions providing enhanced lather while retaining structure using simple, but unexpected, ratios of soap as provided by applicants' claimed invention.

The present invention is the result of experimentation investigating the use of different fatty acids in varying amounts as an alternative to synthetic surfactants to improve lathering properties while maintaining structuring properties. Surprisingly, soap bars with superior lathering which retained structuring properties can be obtained.

The compositions of the present invention have shown to yield, bars with substantially improved lather volume performance in respect to total volume.

BRIEF DESCRIPTION OF THE INVENTION

Quite unexpectedly, applicants have found that using spec ilk blends of fatty acid soaps, wherein minimum amounts of $C_8$-$C_{10}$ soaps are used; ratios of $C_8$-$C_{10}$ to $C_{12}$ soaps are in defined ranges; and maximum amount of $C_{14}$ soap is used; it is possible to make soap bars with enhanced lather while retaining structure relative to other soap blends. The soap bar of the present invention may be extruded or cast-melt.

Specifically, the invention comprises a soap bar composition comprising:
   a) a fatty acid soap blend in an amount of 30 to 90% by wt. of the soap bar comprising:
      (i) caprylic ($C_8$), pelargonic ($C_9$) and capric ($C_{10}$) acids, their salts or their mixtures thereof in an amount of 0.1 to 40 wt. preferably 10 to 40 wt. % of the fatty acid soap blend;
      (ii) myristic acid ($C_{14}$) in amount not higher than 8 wt. % preferably no higher than 4 wt. % of the fatty acid soap blend;
   b) co-adjuvants selected from polyols, polymers, organic and inorganic adjuvants, electrolytes, benefit agents and other minor ingredients in an amount from 0.1 to 50% by weight of the soap composition;
   c) the remainder of water.
wherein the fatty acid blend comprises a ratio of the sum of caprylic, pelargonic and capric acids to lauric acid, ($\Sigma C_{8-10}/C_{12}$), of 0.19 to 2.5, more preferably from 0.5 to 2.0 and more preferably from 0.9 to 1.5.

Specifically, applicants have found that these formulations provide compositions having enhanced hither volume relative to compositions where these criteria are not kept (e.g. C14 is not minimized and ratios of $C_8$-$C_{10}$ to $C_{12}$ are not properly balanced).

DETAILED DESCRIPTION OF THE INVENTION

The present invention relates to a soap bar composition comprising:

a) a fatty acid soap blend in an amount of 30 to 90% by wt. of the soap bar comprising:
   (i) caprylic, pelargonic and capric acids, their salts or their mixtures thereof in an amount of 0.1 to 40 wt. %, preferably 10 to 40 wt. % of the fatty acid soap blend;
   (ii) myristic acid in amount not higher than 8 wt. % of the fatty acid soap blend;
b) co-adjuvants selected from polyols, polymers, organic and inorganic adjuvants, electrolytes, benefit agents and other minor ingredients in an amount from 0.1 to 50% by weight of the soap composition;
c) the remainder of water.
wherein the fatty acid blend comprises a ratio of the sum of caprylic, perlagonic and capric acids to lauric acid, ($\Sigma C_{8-10}/C_{12}$), of 0.19 to 2.5, more preferably from 0.5 to 2.0 and more preferably from 0.9 to 1.5.

Soap Bar Composition

The present invention relates to extruded or melt cast personal washing bars that comprise specific levels and ratios of various fatty acid soaps; optionally one or more added polyols, polymers, organic and inorganic adjuvant materials, electrolytes, benefit agents and other minor ingredients and the remainder of water. These components of the bar composition that are used to manufacture and evaluate the bars are described below. The bar compositions of the invention are capable of being manufactured by processes that generally involve the extrusion forming of ingots or billets, and stamping or molding of these billets into individual tablets, cakes, or bars and alternatively the products can be obtained by the melt cast process.

Fatty Acid Soap Blend

The fatty acid soaps, other surfactants and in fact all the components of the bar should be suitable for routine contact with human skin and preferably yield bars that are high lathering, The present invention relates to a soap bar composition with unproved lather volume which comprises fatty acid blend soap in an amount of 30 to 90% by wt. of the soap bar. More preferably, the fatty acid blend comprises a fatty acid blend in an amount of 40 to 80% by wt. of the soap bar. Most preferably, the fatty acid blend comprises a fatty acid blend in an amount of 45 to 78% by wt. of the soap bar.

The fatty acid blend comprises one or more surfactants. The preferred type of surfactant is fatty acid soap. The term "soap" is used herein in its popular sense, i.e., the alkali metal or alkanol ammonium salts of aliphatic, alkanes, or alkene monocarboxylic acids. Sodium, potassium, magnesium, mono-, di- and tri-ethanol ammonium cations, or combinations thereof, are the most suitable for purposes of this invention. In general, sodium soaps are used in the compositions of this invention, but up to about 15% of the soap may be potassium, magnesium or triethanolamine soaps. The soaps useful herein are the well known alkali metal salts of natural or synthetic aliphatic (alkanoic or alkenoic) acids having about 8 to about 24 carbon atoms. They may be described as alkali metal carboxylates of saturated or unsaturated hydrocarbons having about 8 to about 24 carbon atoms.

The fatty acid blend is made from fatty acids that may be different fatty acids, typically fatty acids containing fatty acid moieties with chain lengths of from $C_8$ to $C_{24}$. The fatty acid blend may also contain relatively pure amounts of one or more fatty acids. Suitable fatty acids include, but are not limited to, butiric, caproic, caprylic, capric, myristic, myristelaidic, pentadecanoic, palmitic, palmitoleic, margaric, heptadecenoic, stearic oleic, linoleic, linolenic, arachidic, gadoleic, behenic and lignoceric acids and their isomers, in a preferred embodiments, the fatty acid blend has fatty acids with fatty acids moiety chains length of 10 (capric acid) and 12 (Jamie acid) carbon atoms. In preferred embodiments, the fatty acid blend has low levels of fatty acid with saturated fatty acid moiety chain length of 14 carbon atoms (myristic acid).

The fatty acid blend of the present invention comprises relatively high amounts (e.g. at least 3%, preferably at least 10%) of capric and lauric acids. Moreover, the invention requires from about 25 to about 55% of unsaturated long chain fatty acids ($C_{18:1}$ and $C_{18:2}$). Additionally the fatty acid blend comprises low levels of myristic acid, (e.g. preferably less than 4% by wt.) which, according to the invention, determines the good lathering properties of the resultant soap bar composition.

In a preferred embodiment, the fatty acid blend may have a proportion of capric acid to lauric acid ranging from 0.5 to 1 to 1.5 to 1.

The fatty acids may be eventually in the form of free fatty acids, preferably in an amount not higher than 5% of the fatty acid soap blend.

Organic and Inorganic Adjuvant Materials

The total level of the adjuvant materials used in the bar composition should be in an amount not higher than 50% by wt. of the soap bar composition.

Suitable starchy materials include natural starch (from corn, wheat, rice, potato, tapioca and the like), pregelatinzed starch, various physically and chemically modified starch and mixtures thereof. By the term natural starch is meant starch which has not been subjected to chemical or physical modification—also known as raw or native starch.

A preferred starch is natural or native starch from maize (corn), cassava, wheat, potato, rice and other natural sources of it. Raw starch with different ratio of amylose and amylopectin: e.g. maize (25% amylose); waxy maize (0%); high amylose maize (70%); potato (23%); rice (16%); sago (27%); cassava (18%); wheat (30%) and others. The raw starch can be used directly or modified during the process of making the bar composition such that the starch becomes gelatinized, either partially or fully gelatinized.

Another suitable starch is pre-gelatinized which is starch that has been gelatinized before it is added as an ingredient in the present bar compositions. Various forms are available that will gel at different temperatures, e.g., cold water dispersible starch. One suitable commercial pre-gelatinized starch is supplied by National Starch Co. (Brazil) under the trade name FARMAL CS 3400 but other commercially available materials having similar characteristics are suitable.

Polyol

Another organic adjuvant could be a polyol or mixture of polyols. Polyol is a term used herein to designate a compound having multiple hydroxyl groups (at least two, preferably at least three) which is highly water soluble, preferably freely soluble, in water.

Many types of polyols are available including: relatively low molecular weight short chain polyhydroxy compounds such as glycerol and propylene glycol; sugars such as sorbitol, manitol, sucrose and glucose: modified carbohydrates such as hydrolyzed starch, dextrin and maltodextrin, and polymeric synthetic polyols such as polyalkylene glycols, for example polyoxyethylene glycol (PEG) and polyoxypropylene glycol (PPG).

Especially preferred polyol are glycerol, sorbitol and their mixtures.

The level of polyol is critical in forming a thermoplastic mass whose material properties are suitable for both high speed manufacture (300-400 bars per minute) and for use as a personal washing bar. It has been found that when the polyol level is too low, the mass is not sufficiently plastic at the extrusion temperature (e.g., 40° C. to 45° C.) and the bars tend to exhibit higher mushing and rates of wear. Conversely, when the polyol level is too high, the mass becomes too soft to be formed into bars by high speed at normal process temperature.

The adjuvant system may optionally include insoluble particles comprising one or a combination of materials. By insoluble particles is meant materials that are present in solid particulate form and suitable for personal washing.

The insoluble particles should not be perceived as scratchy or granular and thus should have a particle size less than 300 microns, more preferably less than 100 microns and most preferably less than 50 microns.

Preferred inorganic particulate material includes talc and calcium carbonate. Talc is a magnesium silicate mineral material, with a sheet silicate structure and a composition of Mg3Si4 (OH)22, and may be available in the hydrated form. It has a plate-like morphology, and is essentially oleophilic/hydrophobic, i.e., it is wetted by oil rather than water.

Calcium carbonate or chalk exists in three crystal forms: calcite, aragonite and vaterite. The natural morphology of calcite is rhombohedral or cuboidal, acicular or dendritic for aragonite and spheroidal for vaterite.

Commercially, calcium carbonate or chalk known as precipitated calcium carbonate is produced by a carbonation method in which carbon dioxide gas is bubbled through an aqueous suspension of calcium hydroxide. In this process the crystal type of calcium carbonate is calcite or a mixture of calcite and aragonite.

Examples of other optional insoluble inorganic particulate materials include alumnio silicates, aluminates, silicates, phosphates, insoluble sulfates, borates and clays (e.g., kaolin, china clay) and their combinations.

Organic particulate materials include: insoluble polysaccharides such as highly crosslinked or insolubilized starch (e.g., by reaction with a hydrophobe such as octyl succinate) and cellulose; synthetic polymers such as various polymer lattices and suspension polymers; insoluble soaps and mixtures thereof.

The structuring system can comprise up to 10% insoluble particles, preferably 5% to 8%, based on the total weight of the bar composition.

Optional Ingredients
Synthetic Surfactants:

The bar compositions can optionally include non-soap synthetic type surfactants (detergents)—so called syndets. Syndets can include anionic surfactants, nonionic surfactants, amphoteric or zwitterionic surfactants and cationic surfactants.

The level of synthetic surfactant present in the bar is generally less than 25%, preferably less than 15%, preferably up to 10%, and most preferably from 0 to 7% based on the total weight of the bar composition.

The anionic surfactant may be, for example, an aliphatic sulfonate, such as a primary alkane (e.g., $C_8$-$C_{22}$) sulfonate, primary alkane (e.g. $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or an aromatic sulfonate such as alkyl benzene sulfonate. Alpha olefin sulfonates are another suitable anionic surfactant.

The anionic may also be an alkyl sulfate (e.g., $C_{12}$-$C_{18}$ alkyl sulfate), especially a primary alcohol sulfate or an alkyl ether sulfate (including alkyl glyceryl ether sulfates).

The anionic surfactant can also be a sulfonated fatty acid such as alpha sulfonated tallow fatty acid, a sulfonated fatty acid ester such as alpha sulfonated methyl tallowate or mixtures thereof.

The anionic surfactant may also be alkyl sulfosuccinates (including mono- and dialkyl e.g., $C_6$-$C_{22}$ sulfosuccinates); alkyl and acyl taurates, alkyl and acyl sarcosinates, sulfoacetates, $C_8$-$C_{22}$ alkyl phosphates and phosphates, alkyl phosphate esters and alkoxyl alkyl phosphate esters, acyl lactates or lactylates, $C_8$-$C_{22}$ monoalkyl succinates and maleates, sulphoacetates, and acyl isethionates.

Another class of anionics is $C_8$ to $C_{20}$ alkyl ethoxy (1-20 EO) carboxylates.

Another suitable anionic surfactant is $C_8$-$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms. The acyl isethionate may also be alkoxylated isethionates Acyl isethionates, when present, will generally range from about 0.5% to about 25% by weight of the total composition.

In general, the anionic component will comprise the majority of the synthetic surfactants used in the bar composition.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. Suitable amphoteric surfactants include amphoacetates, alkyl and alkyl amido betaines, and alkyl and alkyl amido sulphobetaines.

Amphoacetates and diamphoacetates are also intended to be covered in possible zwitterionic and/or amphoteric compounds which may be used.

Suitable nonionic surfactants include the reaction products of compounds having a hydrophobic group and a reactive hydrogen atom, for example aliphatic alcohols or fatty acids, with alkylene oxides, especially ethylene oxide either alone or with propylene oxide. Examples include the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as alkyl polysaccharides and alkyl polysaccharide amides.

Examples of cationic detergents are the quaternary ammonium compounds such as a alkyldimethylammonium halides.

Other surfactants which may be used are described in U.S. Pat. No. 3,723,325 to Parran Jr. and "Surface Active Agents and Detergents" (Vol. I & II) by Schwartz, Perry & Berth, both of which is also incorporated into the subject application by reference.

Finishing Adjuvant Materials:

These are ingredients that improve the aesthetic qualities of the bar especially the visual, tactile and olefactory properties either directly (perfume) or indirectly (preservatives). A wide variety of optional ingredients can be incorporated in the bar composition of the invention. Examples of adjuvants include but are not limited to: perfumes; opacifying agents such as fatty alcohols, ethoxylated fatty acids, solid esters, and $TiO_2$; dyes and pigments; pearlizing agent such as $TiO_2$ coated micas and other interference pigments; plate like mirror particles such as organic glitters; sensates such as menthol and ginger; preservatives such as dimethyloldimethylhydantoin (Glydant XL1000), parabens, sorbic acid and the like; antioxidants such as, for example, butylated hydroxytoluene (BHT); chelating agents such as salts of ethylene diamine tetra acetic acid (EDTA) and trisodium etridronate; emulsion stabilizers; auxiliary thickeners; buffering agents; and mixtures thereof.

The level of pearlizing agent should be between about 0.1% to about 3%, preferably between 0.1% and 0.5% and most preferably between about 0.2 to about 0.4% based on the total weight of the bar composition.

Skin Benefit Agents:

A particular class of optional ingredients highlighted here is skin benefit agents included to promote skin and hair health and condition. Potential benefit agents include but are not limited to: lipids such as cholesterol, ceramides, and pseudoceramides; antimicrobial agents such as TRICLOSAN; sunscreens such as cinnamates; other types of exfoliant particles such as polyethylene beads, walnut shells, apricot seeds, flower petals and seeds, and inorganics such as silica, and pumice; additional emollients (skin softening agents) such as long chain alcohols and waxes like lanolin; additional moisturizers; skin-toning agents; skin nutrients such as vitamins like Vitamin C, D and E and essential oils like bergamot, citrus unshiu, calamus, and the like; water soluble or insoluble extracts of avocado, grape, grape seed, myrrh, cucumber, watercress, calendula, elder flower, geranium, linden blossom, amaranth, seaweed, gingko, ginseng, carrot; impatiens balsamina, camu camu, alpina leaf and other plant extracts such as witch-hazel, and mixtures thereof.

The composition can also include a variety of other active ingredients that provide additional skin (including scalp) benefits. Examples include anti-acne agents such as salicylic and resorcinol; sulfur-containing D and L amino acids and their derivatives and salts, particularly their N-acetyl derivatives; anti-wrinkle, anti-skin atrophy and skin-repair actives such as vitamins (e.g., A, E and K), vitamin alkyl esters, minerals, magnesium, calcium, copper, zinc and other metallic components; retinoic acid and esters and derivatives such as retinal and retinol, vitamin B3 compounds, alpha hydroxy acids, beta hydroxy acids, e.g. salicylic acid and derivatives thereof, skin soothing agents such as aloe vera, jojoba oil, propionic and acetic acid derivatives, fenamic acid derivatives; artificial tanning, agents such as dihydroxyacetone; tyrosine; tyrosine esters such as ethyl tyrosinate and glucose tyrosinate; skin lightening agents such as aloe extract and niacinamide, alpha-glyceryl-L-ascorbic acid, aminotyroxine, ammonium lactate, glycolic acid, hydroquinone, 4 hydroxyanisole, sebum stimulation agents such as bryonolic acid, dehydroepiandrosterone (DHEA) and orizano; sebum inhibitors such as aluminum hydroxy chloride, corticosteroids, dehydroacetic acid and its salts, dichlorophenyl imidazoldioxolan (available from Elubiol); anti-oxidant effects, protease inhibition; skin tightening agents such as terpolymers of vinylpyrrolidone, (meth) acrylic acid and a hydrophobic monomer comprised of long chain alkyl (meth)acrylates; anti-itch agents such as hydrocortisone, methdilizine and trimeprazine hair growth inhibition; 5-alpha reductase inhibitors; agents that enhance desquamation; anti-glycation agents; anti-dandruf agents such as zinc pyridinethione; hair growth promoters such as finasteride, minoxidil, vitamin D analogues and retinoic acid and mixtures thereof.

Electrolyte

The soap bars include 0.5 wt % to 5 wt % electrolyte. Preferred electrolytes include chlorides, sulphates and phosphates of alkali metals or alkaline earth metals. Without wishing, to be bound by theory it is believed that electrolytes help to structure the solidified soap mass and also increase the viscosity of the molten mass by common ion effect. Comparative soap bars without any electrolyte were found to be softer. Sodium chloride and sodium Sulphate are the most preferred electrolyte, more preferably at 0.6 to 3.6 and most preferably at 1.0 to 3.6 wt %.

Polymers

The soap bars may include 0.1 to 5 wt % of a polymer selected from acrylates or cellulose ethers. Preferred acrylates include cross-linked acrylates, polyacrylic acids or sodium polyacrylates. Preferred cellulose ethers include carboxymethyl celluloses or hydroxyalkyl celluloses. A combination of these polymers may also be used, provided the total amount of polymers does not exceed 5 wt %.

Acrylates

Preferred bars include 0.1 to 5% acrylates. More preferred bars include 0.15 to 3% acrylates. Examples of acrylate polymers include polymers and copolymers of acrylic. acid crosslinked with polyallylsucrose as described in U.S. Pat. No. 2,798,053 which is herein incorporated by reference. Other examples include polyacrylates, acrylate copolymers or alkali swellable emulsion acrylate copolymers (e.g, ACULYN® 33 Ex. Rohm and Haas; CARBOPOL® Aqua SF-1 Ex, Lubrizol Inc.), hydrophobically modified alkali swellable copolymers (e.g., ACULYN® 22, ACULYN® 28 and ACULYN® 38 ex. Rohm and Haas). Commercially available crosslinked homopolymers of acrylic acid include CARBOPOL® 934, 940, 941, 956, 980 and 996 carbomers available from Lubrizol Inc. Other commercially available crosslinked acrylic acid copolymers include the CARBOPOL® Ultrez grade series (Ultrez® 10, 20 and 21) and the ETD series (ETD 2020 and 2050) available from Lubrizol Inc.

CARBOPOL® Aqua SF-1 is a particularly preferred acrylate. This compound is a slightly cross-linked, alkali-swellable acrylate copolymer which has three structural units; one or more carboxylic acid monomers having 3 to 10 carbon atoms, one or more vinyl monomers and, one or more mono- or polyunsaturated monomers.

Cellulose Ethers

Preferred bars include 0.1 to 5% cellulose ethers. More preferred bars include 0.1 to 3% cellulose ethers. Preferred cellulose ethers are selected from alkyl celluloses, hydroxyalkyl celluloses and carboxyalkyl celluloses. More preferred bars include hydroxyalkyl celluloses or carboxyalkyl celluloses and particularly preferred bars include carboxyalkyl cellulose.

Preferred hydroxyalkyl cellulose includes hydroxymethyl cellulose, hydroxyethyl cellulose, hydroxypropyl cellulose and ethyl hydroxyethyl cellulose.

Preferred carboxyalkyl cellulose includes carboxymethyl cellulose. It is particularly preferred that the carboxymethyl cellulose is in form of sodium salt of carboxymethyl cellulose.

Wax and Polyalkyleneglycols

Preferred wax includes paraffin wax and microcrystalline wax. When polyalkyleneglycols are used, preferred bars may include 0.01 to 5 wt % Polyalkyleneglycols, more preferably 0.03 to 3 wt % and most preferably 0.5 to 1 wt %. Suitable examples include polyethyleneglycol and polypropyleneglycol. A preferred commercial product is POLYOX® sold by The Dow Chemical Company.

Protocol and Examples

LATHER VOLUME TEST

1. Introduction

The amount of lather generated by a soap bar is an important parameter affecting consumer preference. The lather volume test described herein gives a measure of lather generation under standard conditions, thus allowing objective comparison of different soap formulations.

2. Principle

Lather is generated by trained technicians using a standardised method. The lather is collected and its volume measured.

3. Equipment

| | |
|---|---|
| Washing up bowl | 1 per operator capacity 10 litres |
| Soap drainer dishes | 1 per sample |
| Surgeons' rubber gloves | |
| Tall cylindrical glass beaker | 400 mL, 25 mL graduated (Pyrex n°1000) |
| Thermometer | |
| Glass rod | |

PROCEDURE i. Tablet pre-treatment:
   Wearing the surgeon's glove previously washed in plain soap, wash down all test tablets at least 10 minutes before starting the test sequence. This is best done by twisting them about 20 times through 180 under running water.
ii. Place about 5 liters of water of known hardness and at a specified temperature in a bowl. Change the water after each bar of soap has been tested.
iii. Take up the tablet, dip it in the water and remove it. Twist the tablet 15 times, between the hands, through 180°. Place the tablet on the soap dish.
iv. The lather is generated by the soap remaining on the gloves.
   1: Stage Rub one hand over the other hand (two hands on same direction) 10 times in the same way.
   Stage 2: Grip the right hand with the left, or vice versa, and force the lather to the tips of the fingers.
   This operation is repeated five times.
   Repeat Stages 1 and 2.
   Place the lather in the beaker.
v. Repeat the whole procedure of lather generation from paragraph iii, twice more, combining all the lather in the beaker.
vi. Stir the combined lather gently to release large pockets of air. Read and record the volume.

Data analysis is carried out by two way analysis of variance, followed by Turkey's Test.

EXAMPLES

Solid moisturizing personal wash bars were prepared with different percentages of fatty acids in accordance with the formulations herein below.

The fatty acids used to prepare the formulations are supplied by Cosmoquimica under the commercial Name of Edenor® CS 98/100 (Caprilic acid); Edenor® C10 981100 (Capric acid); Edenor® C12 98/100 (Lauric acid); Edenor® C14 98/100 (Myristic acid); Edenor® C16 98/100 (Palmitic acid); Edenor® C18 98/100 (Stearic acid); Edenor® C1.8:1 98/1.00 (Oleic acid).

Other fatty acids possible suppliers are Quimico Anastácio, Emery Oleochemicals and Aboissa Óleos Vegetais.

TABLE 1

Comparative examples

| Composition | A | B | C | D |
|---|---|---|---|---|
| TFM | 77.88 | 77.88 | 77.88 | 77.88 |
| Sodium Caprylate (C8) | 1.44 | 0.75 | 0.41 | 1.1 |
| Sodium Caprate (C10) | 1.45 | 0.77 | 0.43 | 1.11 |
| Sodium Laurate (C12) | 19.89 | 10.5 | 5.8 | 15.2 |
| ratio ($\Sigma C_{8-10}/C_{12}$) | 0.15 | 0.14 | 0.14 | 0.14 |
| Sodium Myristate (C14) | 7.21 | 4.34 | 2.92 | 5.77 |
| Short saturated:long unsaturated (C18:1 + C18:2) | 35.36 | 36.47 | 36.34 | 36.69 |
| Glycerol | 0.5 | 0.5 | 0.5 | 0.5 |
| Capric Acid (C10) | — | — | — | — |
| Lauric Acid (C12) | — | — | — | — |
| Other Ingredients (%) | up to 100% | up to 100% | up to 100% | up to 100% |
| Lather volume (mL) ± 10 ml | 250 | 220 | 200 | 240 |

| Composition | E | F |
|---|---|---|
| TFM | 77.88 | 76.96 |
| Sodium Caprylate (C8) | — | 0.92 |
| Sodium Caprate (C10) | 1 | 0.7 |
| Sodium Laurate (C12) | 9.5 | 10.12 |
| ratio ($\Sigma C_{8-10}/C_{12}$) | 0.10 | 0.16 |
| Sodium Myristate (C14) | 21.5 | 4.15 |
| Short saturated:long unsaturated (C18:1 + C18:2) | 50 | 36.74 |
| Glycerol | 0.5 | 0.5 |
| Capric Acid (C10) | — | 1 |
| Lauric Acid (C12) | — | — |
| Other Ingredients (%) | up to 100% | up to 100% |
| Lather volume (mL) ± 10 ml | 240 | 260 |

TABLE 2

Invention examples

| Composition | example 1 | example 2 | example 3 | example 4 |
|---|---|---|---|---|
| TFM | 77.88 | 77.88 | 77.88 | 72.20 |
| Sodium Caprylate (C8) | 1.55 | 1.05 | 2.04 | 2.04 |
| Sodium Caprate (C10) | 10.56 | 7.07 | 14.05 | 14.05 |
| Sodium Laurate (C12) | 10.4 | 7.3 | 13.49 | 13.49 |
| ratio ($\Sigma C_{8-10}/C_{12}$) | 1.16 | 1.11 | 1.19 | 1.19 |
| Sodium Myristate (C14) | 1.87 | 1.74 | 2.01 | 2.01 |
| Short saturated:long unsaturated (C18:1 + C18:2) | 36.99 | 36.67 | 35.76 | 35.76 |
| Glycerol | 0.5 | 0.5 | 0.5 | 6.66 |
| Capric Acid (C10) | — | — | — | — |
| Lauric Acid (C12) | — | — | — | — |
| Other Ingredients (%) | up to 100% | up to 100% | up to 100% | up to 100% |
| Lather volume (mL) ± 10 ml | 310 | 280 | 370 | 370 |

| Composition | example 5 | example 6 | example 7 | example 8 |
|---|---|---|---|---|
| TFM | 77.88 | 77.88 | 77.88 | 77.88 |
| Sodium Caprylate (C8) | 0.56 | 19 | 0.3 | 0.0 |
| Sodium Caprate (C10) | 3.58 | 1 | 20 | 12.0 |
| Sodium Laurate (C12) | 4.2 | 8 | 20 | 12.0 |
| ratio ($\Sigma C_{8-10}/C_{12}$) | 0.99 | 2.50 | 1.01 | 1.00 |
| Sodium Myristate (C14) | 1.62 | 4 | 0.4 | 8.0 |
| Short saturated:long unsaturated (C18:1 + C18:2) | 39.1 | 50 | 15 | 50 |
| Glycerol | 0.5 | 0.5 | 0.5 | 0.5 |
| Capric Acid (C10) | — | — | — | — |
| Lauric Acid (C12) | — | — | — | — |
| Other Ingredients (%) | up to 100% | up to 100% | up to 100% | up to 100% |
| Lather volume (mL) ± 10 ml | 230 | 350 | 380 | 340 |

TABLE 3

Examples of compositions with fatty acid blends that include free fatty acids of capric and lauric acids.

| Composition | comparative | comparative | comparative |
|---|---|---|---|
| TFM | 76.96 | 76.04 | 75.12 |
| Sodium Caprylate (C8) | 0.92 | 0.92 | 0.92 |
| Sodium Caprate (C10) | 0.7 | 0.7 | 0.7 |
| Sodium Laurate (C12) | 10.12 | 10.12 | 10.12 |
| Sodium Myristate (C14) | 4.15 | 4.15 | 4.15 |
| Short saturated:long unsaturated (C18:1 + C18:2) | 36.74 | 36.74 | 36.74 |
| Glycerol | 0.5 | 0.5 | 0.5 |
| Capric Acid (C10) | — | 1 | 3 |
| Lauric Acid (C12) | 1 | 1 | — |
| Other Ingredients (%) | up to 100% | up to 100% | up to 100% |
| Lather volume (mL) ± 10 ml | 250 | 270 | 270 |

Comparative examples A to F show typical soap bar compositions currently produced by different manufacturers for which the performance is not as effective as the performance of the formulations described herein. It can be seen that products relatively high amounts of soap blends of myristic acid ($C_{14}$) have relatively lower lather volumes when other short-chain soaps are not balanced in accordance with the invention (e.g., ratio of $C_8$-$C_{10}$/$C_{12}$ at least 0.19. From comparative examples A-F, the impact of myristic acid (C14). or its salt, sodium myristate on the lathering of the soap bar can be seen, if the other short chain fatty acids soaps are not balanced accordingly, as will be shown in table 2. In general, high amounts of such fatty acid decrease the lathering performance reducing the amount of lather produced. Higher levels of myristic acid can only be applied, for example, when the ratios of C8-C10 soaps to lauric (C12) are balanced accordingly, as shown in example 8. Comparative examples D and F show the influence of myristic acid (C14). A slight decrease of myristic acid (C14), from 5.77 in Example D, to 4.15 in Example F is enough to increase lather from 240 to 260 milliliters. The maximum amount of soaps of myristic acid that yield bars with good performance has been determined to be 8.0%.

Without being bound by theory, it is believed that the myristic (C14) acid, or its salt, sodium myristate, have a carbon chain that is not short enough for producing lather and is not long enough for crystallizing together with the other long saturated soaps of fatty acids, thus disturbing the surfactant system in a fashion that depletes its lathering. On the other hand, short chain fatty acids—from caprylic (C8) to lauric (C12) acids have a smaller carbon chain that does not disturb the lathering effect and thus perform well to create bubbles and lather in high amounts.

Additionally, high amounts of caprylic (C8) and capric (C10) acids renders good to optimum lathering properties, specially lather volume, Comparative Example B has comparable amount of myristic acid (C14), 4.34%, to Example 6, 4%. In Example 6, the amount: of caprylic acid (C8) is 19%, which is nearly 20 times higher than the amount in Comparative. This translates to amounts of lather substantially higher, i.e. 240 ml in Example 4 and 350 ml in Example 12.

Capric acid (C10) also plays an important role in generating high amounts of volume of lather, Comparative A has low amounts at Capric acid (C10), only 1.45%. Example 1 shows a substantial amount of Capric acid (C10), 10.56% and higher lather volume, i.e. from 250 ml from Example 1 to 310 ml of lather in Example 1.

It has been found that when the fatty acid blend comprises a ratio of the sum of caprylic, perlagonic and capric acids ($\Sigma C_{8-10}$) to lauric acid ($C_{12}$) of between 0.19 to 2.5, the lather volume increases by ca. 40-50% when compared to conventional soaps. When one compares the examples in Table 1 with those in Table 2 it can see that the ratio of the sum of caprylic, perlagonic and capric acids to lauric acid ($\Sigma C_{8-10}/C_{12}$) in these examples varies substantially. In the comparative examples in Table 1 the ratio ranges from 0.10 to 0.16, presenting, an average lather volume of 235 ml; whereas in the invention examples 3 to 8, the ratio ranges from 0.99 to 2.5, yielding products with average lather volumes as high as 330 mL. In this sense the ratio ($\Sigma C_{8-10}/C_{12}$) is a significant predictor of high amounts of lather for soap bar compositions.

The invention claimed is:

1. Soap bar composition comprising:
   a) a fatty acid soap blend in an amount of 30 to 90% by wt. of the soap bar comprising:
      (i) caprylic, pelargonic and capric acids, their salts or their mixtures thereof in an amount of 0.1 to 40 wt. % of the fatty acid soap blend;
      (ii) myristic acid in amount not higher than 8 wt. % of the fatty acid soap blend;
   b) co-adjuvants selected from polyols, polymers, organic and inorganic adjuvants, electrolytes, benefit agents and other minor ingredients in an amount from 0.1 to 50% by weight of the soap composition;
   c) the remainder of water;
   wherein the fatty acid blend comprises a ratio of the sum of caprylic, perlagonic and capric acids to lauric acid, ($\Sigma C_{8-10}/C_{12}$), of 0.5 to 2.5.

2. A soap bar according to claim 1 wherein the fatty acid blend comprises lauric acid in an amount of 0.1 to 35% by wt. of the fatty acid soap blend.

3. A soap bar according to claim 1 wherein the fatty acid blend comprises the sum of capric, pelargonic and caproic acids in an amount of 10% wt. to 40% wt. of total fatty acids.

4. A soap bar according to claim 1 wherein the fatty acid blend comprises myristic acid in an amount of 1% wt. to about 7% wt. of total fatty acids.

5. A soap bar according to claim 1 wherein said fatty acid blend further comprises a linoleic acid in an amount less than 15% by wt. of total fatty acids.

6. A soap bar according to claim 1, wherein said fatty acid blend further comprises the sum of palmitic and stearic fatty acids in amount of about 7 to about 70% by wt. of total fatty acids blend.

7. A soap bar according to claim 1, wherein said fatty acid blend further comprises 0.01 to about 7% of free fatty acids.

8. A soap bar according to claim 1 producing about 370 ml of lather according to the lather volume test.

9. A bar according to claim 2, wherein ratio of sum of $C_8$-$C_{10}$ to $C_{12}$ is from 0.5 to 2.0.

10. A bar according to claim 2, wherein blend comprises 8 to 16% lauric acid.

11. A bar according to claim 5, wherein linoleic acid in said blend comprises less than 6% of total fatty acid.

12. A bar according to claim 11, wherein linoleic comprises less than 2% of total fatty acid.

13. A bar according to claim 6, wherein sum of palmitic and stearic is 15 to 60% by wt. of total fatty acid.

* * * * *